(12) United States Patent
Lörch et al.

(10) Patent No.: US 6,365,353 B1
(45) Date of Patent: Apr. 2, 2002

(54) METHOD FOR COMPARING THE NUMBER OF REPLICATIONS OF NUCLEIC ACID SEQUENCES

(75) Inventors: Thomas Lörch, Reilingen; Andreas Plesch, Schwetzingen, both of (DE); Jorma Isola, Tampere (FI)

(73) Assignee: Metasystems Hard and Software GmbH, Altlussheim (DE)

( * ) Notice: Subject to any disclaimer, the term of this patent is extended or adjusted under 35 U.S.C. 154(b) by 0 days.

(21) Appl. No.: 09/509,580

(22) PCT Filed: Sep. 30, 1998

(86) PCT No.: PCT/EP98/06219

§ 371 Date: Jun. 12, 2000

§ 102(e) Date: Jun. 12, 2000

(87) PCT Pub. No.: WO99/16901

PCT Pub. Date: Apr. 8, 1999

(30) Foreign Application Priority Data

Sep. 30, 1997 (DE) .......................... 197 43 301

(51) Int. Cl.⁷ .............................. C12Q 1/68; C12Q 1/00; C12P 19/34; C07H 21/02; C07H 21/04
(52) U.S. Cl. .............................. 435/6; 435/4; 435/91.1; 536/23.1; 536/24.3; 536/24.31; 536/24.33
(58) Field of Search .................... 435/6, 91.1; 536/23.1, 536/24.3, 24.31, 24.33

(56) References Cited

U.S. PATENT DOCUMENTS 5,976,790 A  * 11/1999  Pinkel et al. .................. 435/6

FOREIGN PATENT DOCUMENTS

WO          WO 93/18186       * 9/1993

OTHER PUBLICATIONS

Lundsteen et al. "Image analysis and Comparative Genomic Hybridization" Cytometry (1995) 19:42–50.*
Piper et al. "Computer image analysis of Comparative Genomic Hybridization" Cytometry (1995) 19:10–16.*
Bornfleth et al. "Comparative Genomic Hybridization Imaging by the one–chip true–color CCD camera Kappa CF 15 MC" Cytometry (1996) 24(1):1–13.*

* cited by examiner

Primary Examiner—Carla J. Myers
Assistant Examiner—Alexandria H. Spiegler
(74) Attorney, Agent, or Firm—Dority & Manning, PA (57) ABSTRACT

A method is provided for comparing the relative copy number of nucleic sequences of two or more nucleic acid sequence collectives which includes hybridizing differentially labeled i) nucleic acid sequence collectives; ii) a reference nucleic acid sequence collective; and iii) a calibration nucleic acid sequence collective. The method includes determining quotient values for the reference nucleic acid sequence and the calibration nucleic acid sequence and using correction curve calculations to determine a final relative copy number of the nucleic acid sequences of the nucleic acid sequence collective.

14 Claims, 4 Drawing Sheets

METHOD FOR COMPARING THE NUMBER OF REPLICATIONS OF NUCLEIC ACID SEQUENCES

This application is the National Stage of International application No. PCT/EP98/06219, filed Sep. 30, 1998.

BACKGROUND OF THE INVENTION

The invention is relative to a molecular genetic method. The copy number of different nucleic acid sequences of a collective of nucleic acid sequences to be investigated, of a so-called nucleic acid sequence collective is compared with the copy number of a different nucleic acid sequence collective with this method. This comparison determines the changes in the copy number of the nucleic acid sequence collectives relative to one another as well as the sites at which these changes occur.

The nucleic acid sequence collectives described here can be in particular genomes or chromosomes or DNA or RNA sequences from different genomes. The further comments, in as far as they refer to genomes, chromosomes or DNA or RNA sequences, are in no way intended to limit the general concept of the nucleic acid sequence collective but rather are used exclusively to simplify the presentation. Of course, that which is disclosed within the framework of the present invention applies in a general manner to any nucleic acid sequence collectives.

The fluorescence marking of nucleic acids and chromosomes and the subsequent fluorescence microscopic detection have been known since 1970 already from publications of Person and Bobrow.

Even the production of in-situ hybridizations using fluorescence markers is described, for example, in U.S. Pat. No. 5,447,841 EP 430,402 A1 and WO 90/05789. This fluorescence in-situ hybridization is used in particular for analyzing numeric and structural chromosomal anomalies. In this method fluorescence-marked DNA sequences are hybridized onto a DNA to be investigated. The marked DNA settles by recombination on the site of the DNA to be investigated which is complementary to the marked DNA. The hybridized, marked DNA sequences can then be detected with fluorescence-microscopic techniques. This detection of fluorescence markers is carried out on metaphase or interphase nuclei as a function of the question posed. For the case in which the localization of the marked DNA sequences on the corresponding chromosome is significant the metaphase cells are investigated. If, however, the number of marked DNA sequences is to be determined, as, e.g., in the analysis of numeric aberrations of chromosomes, it is sufficient to subject the interphase nuclei to fluorescence-microscopic analysis.

A further development of this technique is comparative genomic hybridization, CGH, which is used in particular in the diagnosing of tumors. In contrast to the method cited above, in this method the isolated DNA of a genome to be investigated is marked with fluorescent dyes. This marked DNA is hybridized together with reference DNA on metaphase chromosomes.

Thus, for example, DNA to be investigated which is isolated from tumor tissue (test DNA) is marked in a fluorescent color (e.g. green). This marked test DNA is then hybridized together with normal reference DNA marked in a different color (e.g. red) onto normal metaphase chromosomes which are marked blue, e.g., with 4, 6-diamidino-2-phenylindol (DAPI). During the recombination during the hybridization a competition takes place between the test DNA and the reference DNA for the binding sites on the DNA of the metaphase cell. Normal ranges of the tumor genome will settle with the same probability on the metaphase chromosomes as the corresponding ranges of the reference DNA. These ranges exhibit a certain intensity ratios of the dyes red and green used in the fluorescence-microscopic evaluation. The areas of the tumor genome which exhibit an increase in the copy number of the DNA sequences recombine with a greater probability than the reference DNA with the sites of the metaphase chromosomes complementary to them so that a shift of the intensity ratio in the direction of green occurs at the corresponding sites. On the other hand, the areas of the test DNA in which the copy number of the DNA sequences is reduced are recognized by a red shift of the intensity ratio. The different fluorescence intensities with which the changes in the copy number of the DNA sequences can be recognized are represented via a quantitative evaluation of the green/red intensity ratios as so-called profiles of the ratio values. In this connection a ratio value represents the standardized quotient from the intensities of the green and of the red fluorescence of a certain DNA sequence.

WO 93/18186 describes a method of comparative genome hybridization. In this method the DNA of a genome to be investigated is marked with fluorescent dyes and hybridized on metaphase chromosomes. The intensity of the fluorescence-microscopic signals of the DNA to be investigated is subsequently measured as a function of the position on the metaphase chromosomes. As a result of the comparison of the intensities at different sites of the genome to be investigated which correspond to different DNA sequences conclusions about the existence of such DNA sequences can be drawn which are present relative to the other DNA sequences of the genome with a changed number of copies.

Systematic deviations from the expected ratio values result in this CGH method. Thus, for example, the following factual situation is regularly found for the X chromosome:

The X chromosome is used as an internal control when female tumor DNA (2 X chromosomes) is mixed with male reference DNA (only one X chromosome) and hybridized on metaphase chromosomes. The expected ratio value should be on the average approximately 2.0 due to the double number of X chromosomes in the test DNA. However, in most hybridizations it is distinctly below that value, approximately only between 1.5 and 1.8. In general, a diminution of the dynamics of the CGH ratio values is observed, that is, the ratio values <1 as well as the ratio values >1 are shifted in direction 1, that is, in the direction of normal value. This dynamic loss results in a reduced sensitivity of the CGH method and rather slight changes in the copy number can no longer be reliably detected since they remain below the significance thresholds. This sharply limits the ability of the CGH results to be interpreted diagnostically, especially if slight variations in the number of copies are involved.

The precise cause of the diminished dynamics of the ratio profiles is not known. A possible explanation for the observed effect might be an insufficient saturation of the non-specific components of the test genomes and reference genomes used. Non-specific components, so-called repetitive sequences, are sites on the genome which comprise frequently occurring DNA sequences and can therefore recombine with various other sequences within the genome. The additive components of this non-specific recombination for test DNA and reference DNA results in a shift of the ratio values in direction 1. During the performance of CGH investigations these repetitive sequences are saturated by non-marked Cot-1-DNA; however, the saturation does not always take place in a complete manner.

The correction of this effect was previously suggested by Lundsteen et al. in that an empirically determined value such as, e.g., 10% is subtracted from the fluorescence intensities measured. However, a significant disadvantage of this empirical correction is the susceptibility to experimental fluctuations. Also, results have shown that such a simple model does not sufficiently describe the observed effects. Karhu et al. show in "Quality Control of CGH: Impact of Metaphase Chromosomes and the Dynamic Range of Hybridization", Cytometry, 28: pp. 198–205, (1997) that the dynamic range of the ratio values for identical text DNA and reference DNA depends heavily on the ability of the metaphase chromosomes on which the hybridization is carried out to be hybridized and does not correlate with customary checking criteria of the suppression of repetitive sequences such as the hybridization intensity of centromeres.

WO 93/18186 also describes in claims 10, 11 and 17 the quantitative determination of a changed number of copies of DNA sequences of the genome in comparison to those of another genome. To this end the DNA of both genomes is marked in different fluorescent dyes and hybridized onto normal metaphase chromosomes. After the measuring of the intensities as a function of their position on the metaphase chromosomes a profile of the ratio values is formed which reflects the relative intensities of the DNA sequences of the genomes used relative to each other at corresponding sites of the genomes. The ratio profile obtained is standardized using a calibrating sequence known on both genomes in order to be able to subsequently convert the unknown sequences via their ratio values into absolute copy numbers. A correction of the experimentally observed diminution of the dynamics of CGH ratio profiles is not possible in this manner. Even the calibration, described there in claim 12, of changes in copy number via the pair-by-pair comparison of more than two simultaneously hybridized genomes serves solely to convert quotients into absolute values.

SUMMARY OF THE INVENTION

The present invention has the problem of indicating a method of comparing the copy number of nucleic acid sequences from different nucleic acid sequence collectives which does not have this diminution of dynamics. Thus, it should be made possible to determine and correct systematic hybridization influences by using an internal standard. Furthermore, the correction should be able to be carried out independently of the nucleic acid sequence collectives to be investigated so that a nucleic acid sequence collective which is completely unknown can be investigated.

To this end the following steps indicate a solution to the problem and are carried out for a comparison of the copy number of nucleic acid sequences of two or more nucleic acid sequence collectives:

DETAILED DESCRIPTION OF THE PREFERRED EMBODIMENTS a) Hybridization of
   i) A nucleic acid sequence collective (T) to be investigated.
   ii) A reference nucleic acid sequence collective (R) and
   iii) At least a further nucleic acid sequence collective with a known deviation in the copy number of the nucleic acid sequences at at least one known site (calibration nucleic acid sequence collective, S), which further nucleic acid sequence collective is as similar as possible to the reference nucleic acid sequence collective,
which nucleic acid sequence collectives are provided with different markings on a collective of suitable target nucleic acid sequences,
  b) Detection of the intensities of the markings of the individual marked nucleic acid sequence collectives hybridized on the target nucleic acid sequences,
  c) Determination of the quotients $Q_R$ of the intensities of the markings of the nucleic acid sequences of the nucleic acid sequence collective to be investigated and the corresponding intensities of the markings of the nucleic acid sequences of the reference nucleic acid sequence collective,
  d) Determination of the quotients $Q_S$ of the intensities of the markings of the nucleic acid sequences of the nucleic acid sequence collective to be investigated and the corresponding intensities of the markings of the nucleic acid sequences of the calibration nucleic acid sequence collective,
  e) Determination of the relative copy numbers, the so-called ratio values, of the nucleic acid sequences to be investigated in comparison to the reference nucleic acid sequences by means of suitable standardization of the quotients $Q_R$ from c),
  f) Determination of the relative copy numbers, the so-called ratio values, of the nucleic acid sequences to be investigated in comparison to the calibration nucleic acid sequences by means of suitable standardization of the quotients $Q_S$ from d),
  g) Determination of at least two support sites corresponding to at least two ratio values of the calibration nucleic acid sequences and of the reference nucleic acid sequences differing from each other in their amount with a known deviation in the copy number of the calibration nucleic acid sequences,
  h) Calculation of a correction curve using the deviations of the ratio values obtained and present at the support sites from the ratio values expected on account of the known changes in the copy number of the calibration nucleic acid sequences, and
  i) Correction of the copy numbers or ratio values obtained under e) with the aid of the correction curve obtained under h).

It is another aspect of the present invention to employ, different fluorescent dyes are used for marking. The marked nucleic acid sequences can be readily detected and evaluated subsequently by measuring their fluorescence-microscopic signals.

However, all other marking types are conceivable.

A further method for determining the relative copy number of nucleic acid sequences of two or more nucleic acid sequence collectives comprising the following steps:
  hybridizing
   i) a nucleic acid sequence collective (T) to be investigated;

ii) a reference nucleic acid sequence collective (R); and iii) at least one calibration nucleic acid sequence collective (S) having a known deviation in the copy number of its nucleic acid sequences at at least one known position in comparison to the copy number at the corresponding position of the nucleic acid sequences of the reference nucleic acid sequence collective, the calibration nucleic acid sequence collective being substantially identical to the reference nucleic acid sequence collective with a collective of suitable target nucleic acid sequences, wherein each of the nucleic acid sequence collectives i) to iii) is provided with a different labeling;

detecting at each position of the nucleic acid sequences the intensity of the labeling of each of the differently labeled nucleic acid sequence collectives i) to iii) being hybridized with the target nucleic acid sequences;

determining for each position a quotient $Q_R$ by dividing the intensity of the labeling of the nucleic acid sequences of the nucleic acid sequence collective to be investigated through the corresponding intensity of the labeling of the nucleic acid sequences of the reference nucleic acid sequence collective;

determining for each position a quotient $Q_S$ by dividing the intensity of the labeling of the nucleic acid sequences of the nucleic acid sequence collective to be investigated through the corresponding intensity of the labeling of the nucleic acid sequences of the calibration nucleic acid sequence collective;

determining uncorrected relative copy numbers (ratio values) of the nucleic acid sequences of the nucleic acid sequence collective to be investigated in comparison to the nucleic acid sequences of the reference nucleic acid sequence collective by means of standardizing the quotients $Q_R$ obtained above by dividing the value of $Q_R$ at each position through the value of $Q_R$ which occurs most frequently over all positions;

determining uncorrected relative copy numbers (ratio values) of the nucleic acid sequences of the nucleic acid sequence collective to be investigated in comparison to the nucleic acid sequences of the calibration nucleic acid sequence collective by means of standardizing the quotients $Q_S$ obtained above by dividing the value of $Q_S$ at each position through the value of $Q_S$ which occurs most frequently over all positions;

determining at least two anchor positions in the nucleic acid sequences of the calibration nucleic acid sequence collective and the reference nucleic acid sequence collective showing a deviation in the amount of the uncorrected ratio values being equal to the known deviation in the copy number of the nucleic acid sequences of the calibration nucleic acid sequence collective at at least the known position in comparison to the copy number at the corresponding position of the nucleic acid sequences of the reference nucleic acid sequence collective;

calculating a correction curve using the deviations between the uncorrected ratio values at the anchor positions obtained above and corresponding ratio values which are expected due to the known deviation in the copy number of the nucleic acid sequences of the calibration nucleic acid sequence collective in comparison to the copy number of the nucleic acid sequences of the reference nucleic acid sequence collective; and, determining final relative copy numbers of the nucleic acid sequences of the nucleic acid sequence collective to be investigated by correcting the uncorrected relative copy numbers with the aid of the correction curve;

wherein the nucleic acid sequence collectives are selected from the group consisting of mRNA, cDNA, genomic DNA, and chromosomal DNA.

In particular, metaphase chromosomes or isolated nucleic acid sequences arranged on a substrate in a defined manner are suitable as collective of the target nucleic acid sequences.

The target nucleic acid sequences may be DNA or cDNA.

The suitable standardization of quotients $Q_R$ and $Q_S$ cited under step f) takes place, for example, by forming the quotients from the values $Q_R$ and $Q_S$ and the values for $Q_R$ and $Q_S$ which occur most frequently on the whole so that the quotient which is standardized the most frequently receives the numeric value 1.0.

This standardization can also be carried out in the following 3 steps:

1) The intensity profiles of the nucleic acid sequences of the nucleic acid sequence collective to be investigated are standardized to an average value of 1.0.

2) The intensity profiles of the nucleic acid sequences of the reference nucleic acid sequence collective are standardized in such a manner that the most frequent ratio value from nucleic acid sequences to be investigated and from reference nucleic acid sequences receives the value 1.0, 3) The intensity profiles of the nucleic acid sequences of the calibration nucleic acid collective are standardized independently in a manner corresponding to that of the nucleic acid sequences of the reference nucleic acid sequence collective.

According to another aspect of this invention, normal female DNA can be used, e.g., as reference nucleic acid sequence collective and a male cell with a trisomy 13 as calibration nucleic acid sequence collective. The theoretical average ratio values from the calibration nucleic acid sequence collective and reference nucleic acid sequence collective for the profiles of two chromosomes are therefore known (X chromosome:0.5, chromosome 13:1.5). The actual ratio values differ on account of the deviation of dynamics. The correction terms can be calculated from the known ratio values of chromosome 13 and X as well as from the average ratio value for all other chromosomes present in the calibration nucleic acid sequence collective in normal copy number which value is always 1.0 on account of the standardization and applied to the ratio values obtained from the measured intensity profiles in order to improve in this manner the reproducibility and sensitivity of the CGH method.

In this connection the following meanings are associated with the signs used:

$t_i$ The measured value of the test DNA intensity profile at position i $r_i$ The measured value of the reference DNA intensity profile at position i $s_i$ The measured value of the calibration DNA intensity profile at position i $t'_i$ The corrected value of the test DNA intensity profile at position i $r'_i$ The corrected value of the reference DNA intensity profile at position i $s'_i$ The corrected value of the calibration DNA intensity profile at position i $q_i$ The value of the ratio profile at position i $q'_i$ The corrected value of the ratio profile at position i
A,B,C,M, $A_X, A_{13}, M_X, M_{13}$: The correction terms calculated according to the following algorithms.

I Additive Correction from X Chromosome

This correction starts with an elevation of all measured hybridization intensities (based on, e.g., incompletely suppressed repetitive sequences), which shifts all ratio values in the direction of 1.0 and as a result reduces the dynamics of the ratio profiles. This can be corrected by an additive correction of the individual intensity profiles before the calculation of the ratio. The correction formula is:

$$t'_i = t_i + A$$

$$r'_i = r_i + A.$$

The ratio values are calculated the aid of the corrected profile values:

$$q'_i = t'_i / r'_i.$$

Since the corrected ratio value for the X chromosome must be equal to the theoretical value 0.5, $$0.5 = s'_X / r'_X = (s_X + A)/(r_X + A)$$

$$A = r_X - 2s_X$$

follows for the correction term A.

II Multiplicative Correction from the X Chromosome

This correction method starts from the fact that the dynamic range of the ratio profiles is reduced by a multiplicative factor of M which shifts the ratio values closer to the value 1.0. The value 1.0 is again always correct on account of the standardization. The correction formula for the multiplicative factor M turns out to be:

$$(q'_i - 1) = M(q_i - 1)$$

or $$q'_i = M(q_i - 1) + 1.$$

$$0.5 = M(s_X / r_X - 1) + 1$$

$$M = r_X / 2(r_X - s_X)$$

follows from the known ratio value for calibration-and reference nucleic acid sequences of the X chromosome.

III Quadratic Correction from Chromosomes X, 13

In this correction statement a linear, quadratic relationship is assumed between determined and theoretical ratio values. The correction formula is:

$$q'_i = A\ q_i^2 + B\ q_i + C.$$

$$1 = A + B + C$$

is valid on account of the standardization (the corrected ratio value for 1 is 1).

The known ratio values for calibration-and reference nucleic acid sequences of chromosomes X and 13 define two additional relationships:

$$0.5 = A(s_X/r_X)^2 + B(s_X/r_X) + C$$

$$1.5 = A(s_{13}/r_{13})^2 + B(s_{13}/r_{13}) + C.$$

Solving this linear system of three equations yields the coefficients A, B and C. If a calibration nucleic acid sequence collective is used that comprises further different copy numbers and ratio values in addition to the ratio values 0.5, 1.0 and 1.5, additional support sites for calculating the correction curve result. Correction curves of the third or of a higher order can then be calculated from the resulting equation system of 4 or more ratio support sites which correction curves make possible an even more precise dynamic correction.

IV Minimal Additive Correction from Chromosomes X, 13

This algorithm calculates an additive correction factor from the X chromosome and calculates a second, independent correction factor from chromosome 13 and uses the smaller correction factor as a conservative estimate to avoid overcorrecting. The correction formula results as (see also I):

$$t'_i = t_i + A$$

$$r'_i = r_i + A.$$

The correction term $A_X$ from the ratio value of the X chromosome is (see I):

$$0.5 s'_X / r'_X = (s_X + A_X)/(r_X + A_X)$$

$$A_X = r_X - 2s_X.$$

The following is valid for the correction term $A_{13}$ derived from chromosome 13:

$$1.5 = s'_{13}/r'_{13} = (s_{13} + A_{13})/(r_{13} + A_{13})$$

$$A_{13} = 2s_{13} - 3r_{13}.$$

The correction uses the smaller amount of the two values $A_X$ and $A_{13}$ in order to avoid an overcorrection.

V Minimal Multiplicative Correction from Chromosomes X, 13

Two independent correction factors $M_X$ and $M_{13}$ are determined from chromosomes X and 13 in analogy with the procedure at II of which factors the one with the smaller amount is used for the correction in order to avoid an overcorrection.

In addition to the dynamic correction of the CGH profiles the normal ratio values for reference-and calibration nucleic acid sequences yield information about the reproducibility and constancy of the hybridization and about the differential ability to hybridize on individual ranges of the target nucleic acid sequences. This information serves to recognize ranges which have hybridization problems with an increased probability such as, e.g.,1ptr, 19 and 22 of the chromosomes and to appropriately take them into consideration when interpreting the results.

Although the algorithms were depicted by way of example for a correction using the entire chromosomes X and 13, it is obvious that the correction curves could be determined in an analogous fashion using the ratio profiles of chromosomal ranges altered in their copy number instead of entire chromosomes. In this instance instead of the ratio profiles of the entire chromosomes X and 13 the appropriate ratio profiles of known, aberrant chromosomal ranges were taken as the basis for the calculation.

The following example is cited in this regard: If a calibration nucleic acid sequence collective is used that comprises known copy number changes of the p arm of chromosome 1 and of the q arm of chromosome 12, then the values X and 13 would have to be replaced by 1p and 12q and, if necessary, 0.5 and 1.5 by the current copy number changes of chromosomal ranges 1p and 12q of the calibration nucleic acid sequence collective. This does not affect the basic correction statement.

The invention can also be used with advantage for CGH investigations of DNA arrays instead of metaphase chromosomes as hybridization target. Such DNA arrays are described in DE 4344 726 A1 and replace metaphase chromosomes with a defined arrangement of isolated nucleic acid sequences on a suitable substrate which can correspond to certain chromosomes or chromosome sections down to individual genes. These defined arrangements include isolated nucleic acid sequences arranged on a substrate in a defined manner and are used as a collective of the target nucleic acid sequences. Said arrays can be used with particular advantage for increasing the local resolution of the CGH method and simplifying the automatization of the evaluation. The ability of the DNA arrays to be hybridized is very sharply reduced in comparison to metaphase chromosomes by the separate arrangement of the nucleic acid sequences distributed over a relatively large surface. Also, the evaluation of the hybridization quality is much more difficult than in the metaphase-or chromosome context. An internal control and, if necessary, correction of the ability of the individual targets to be hybridized is therefore of particular significance in this method, especially if slight changes in the copy number are to be determined.

More than two ratio values differing in their amounts from each other are used here in step g) as support sites in order to make possible the calculation of higher-order correction curves. This development of the method in accordance with the invention has already been mentioned in the description of algorithms I to V used.

In a borderline case a calibration genome could be used as calibration nucleic acid sequence collective which calibration genome comprises numeric aberrations known for several chromosomal ranges. In this case, however, the total number of the aberrant chromosomal ranges in the calibration genome is to be limited in such a manner that the ratio value which occurs most frequently corresponds to the normal copy number. This limitation is necessary in order that a standardization of the ratio values can be carried out. Such a multiply aberrant calibration genome which could contain monosomies and trisomies of entire chromosomes or also of chromosomal ranges would additionally simplify the classification of chromosomes which are difficult to distinguish. Even deviations in the dynamic change of ratio profiles between individual chromosome classes could be recognized with such a calibration genome. This, for its part, results in correspondingly more known ratio profiles which on the one hand permit further statements about reproducibility and the precision of the measurement carried out and on the other hand make possible an individual dynamic correction of individual chromosome classes. It is especially advantageous in this connection that even individual, frequently deviating chromosome classes are recognized and corrected and can be excluded from the investigation.

Furthermore, the ratio values expected in step h) due to the known changes in the copy number of the calibration nucleic acid sequences cannot be associated with one ratio value obtained but rather with the average value of different ratio values obtained which were obtained from different sequences of the calibration-and the reference nucleic acid sequences with the same ratio values to be expected. Statistical or systematic chromosome-dependent hybridizing influences are also reduced by using the average value of several ratio values for the individual support sites for determining the correction curve.

The suppression of the repetitive sequences may occur in that before the hybridization the repetitive sequences of the nucleic acid sequences, reference nucleic acid sequences and calibration nucleic acid sequences to be investigated are removed to a great extent. Refer in this regard to the methods known from the state of the art, e.g., in U.S. Pat. No. 5,447,841.

Alternatively, before the hybridization the repetitive sequences of the nucleic acid sequences, reference nucleic acid sequences and calibration nucleic acid sequences or the repetitive sequences of the target nucleic acid sequences to be investigated can be blocked to a great extent by being saturated with Cot-1-DNA. This Cot-1-DNA can be obtained from Bethesda Research Laboratory (Gaithersburg, Md, USA), among other places. In addition, it is possible according to the present invention that the repetitive sequences of the nucleic acid sequences, reference nucleic acid sequences and calibration nucleic acid sequences or the repetitive sequences of the target nucleic acid sequences to be investigated are blocked to a great extent with Cot-1-DNA during the hybridization.

These methods are described, for example, in "Optimizing Comparative Genomic Hybridization for Analysis of DNA Sequence Copy Number Changes in Solid Tumors" by Kallionimi et al, Genes, Chromosomes & Cancer, vol. 10, pp. 231 to 243 (1994) or in "Image Analysis and Comparative Genomic Hybridization" by Lundsteen et al, Cytometry, vol. 19,pp. 42 to 50 (1995).

The method steps set forth therein of marking, hybridization and the detection of the intensities of the markings, e.g., by means of fluorescence-microscopic methods as well as regarding the method steps of an isolation and amplification which may have to be performed beforehand to the methods known from the state of the art, e.g., from U.S. Pat. No. 5,447,841 or WO 93/18186.

An advantageous development of the method in accordance with the invention is also constituted by the mentioned amplification of the nucleic acid sequences of the nucleic acid sequence collective to be investigated and of the reference-and calibration nucleic acid sequence collective before the marking.

According to another aspect of this invention the correction curves can also be calculated specifically for individual chromosomes or chromosome ranges if a calibration nucleic acid sequence collective is used that comprises known copy number changes for several chromosomes or chromosome ranges. The chromosomes or chromosome ranges are then corrected individually using the specific correction curves. Thus, the dynamic correction could also compensate chromosome- specific dynamic changes.

It is also an advantageous development of the method in accordance with the invention if the calibration nucleic acid sequences have changes in the copy number in the form of numeric chromosomal aberrations.

Furthermore, it is advantageous to produce the calibration nucleic acid sequences by mixing libraries of entire chromosomes or chromosome ranges.

An additional advantage development includes that the known changes in the copy number of the calibration nucleic acid sequences are located at suitable sites. The intensities of individual chromosomes and/or chromosome ranges can be used, e.g., in a karyogram for distinguishing chromosomes.

The invention is described in the following in an exemplary manner without limiting the general concept of the invention, using exemplary embodiments and referring to FIGS. 1 to 3*b* to which figures express reference is made regarding the disclosure of all particulars of the invention not explained in detail in the text.

Table 1 shows by way of example the reduced dynamics of the ratio values of three CGH experiments. The calibration nucleic acid sequence collective (male, trisomy 13) was marked with the dye Cy5 and the reference nucleic acid sequence collective (female, normal) with the dye Texas Red. Instead of the theoretical ratio values for X chromosome and chromosome 13 of 0.5 and 1.5 values between 0.64 and 0.7 and between 1.35 and 1.42 were determined.

TABLE 1

| Experiment | Av. ratio chr. X (No. metaphases) | Deviation | Av. ratio chr. 13 | Deviation |
|---|---|---|---|---|
| A | 0.70 (7) | 0.20 | 1.37 | 0.13 |
| B | 0.64 (3) | 0.14 | 1.31 | 0.19 |
| C | 0.64 (6) | 0.14 | 1.35 | 0.15 |

Figure 1:
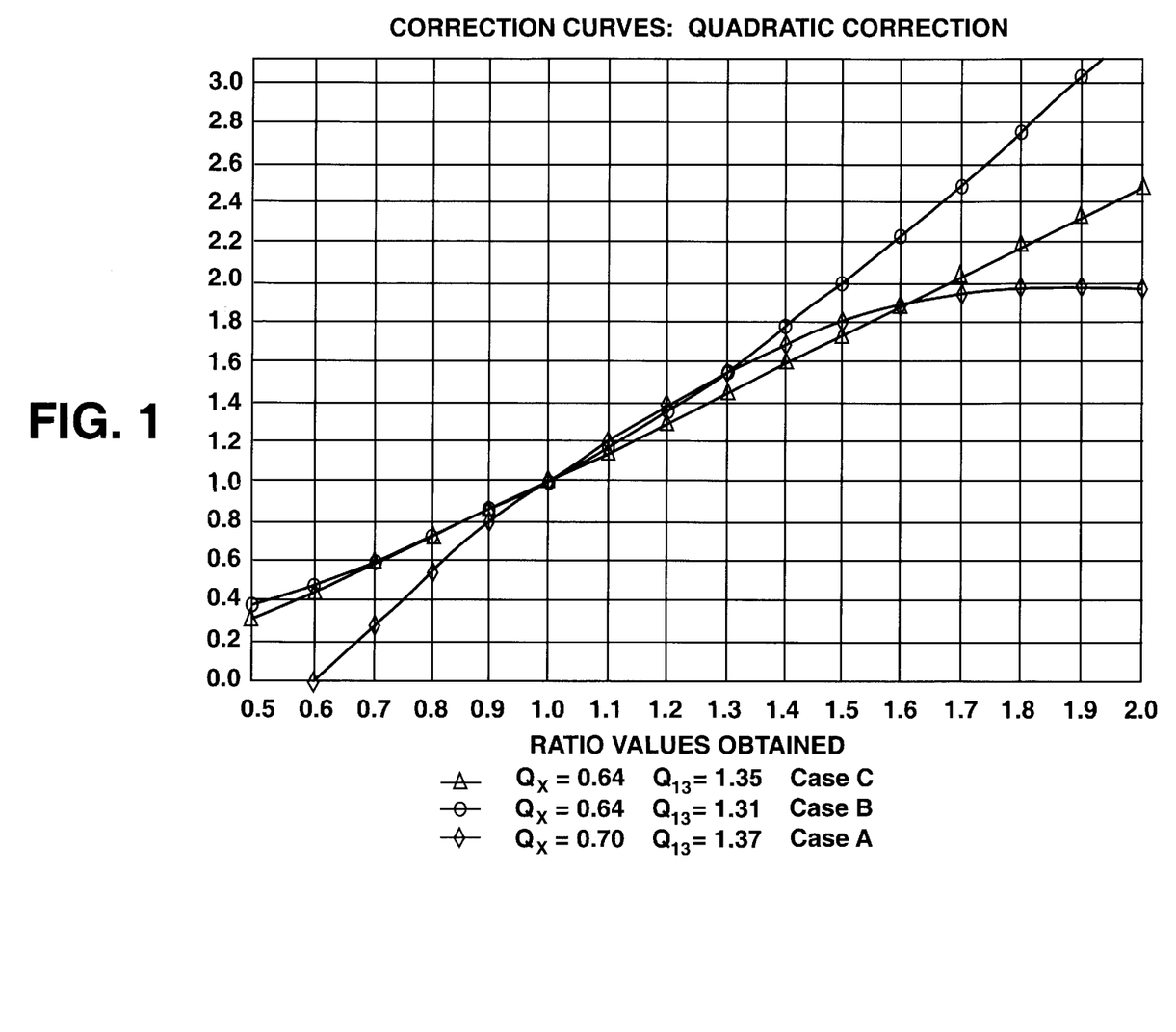
FIG. 1 sets forth a correction curve for the data set forth in Table 1.

FIG. 1 shows the correction curves which result for the experiments in table 1 when using a quadratic correction (see III). As a result of the standardization of the measured ratio profiles the correction curves always intersect at the point (1.0/1.0).

Figure 2:
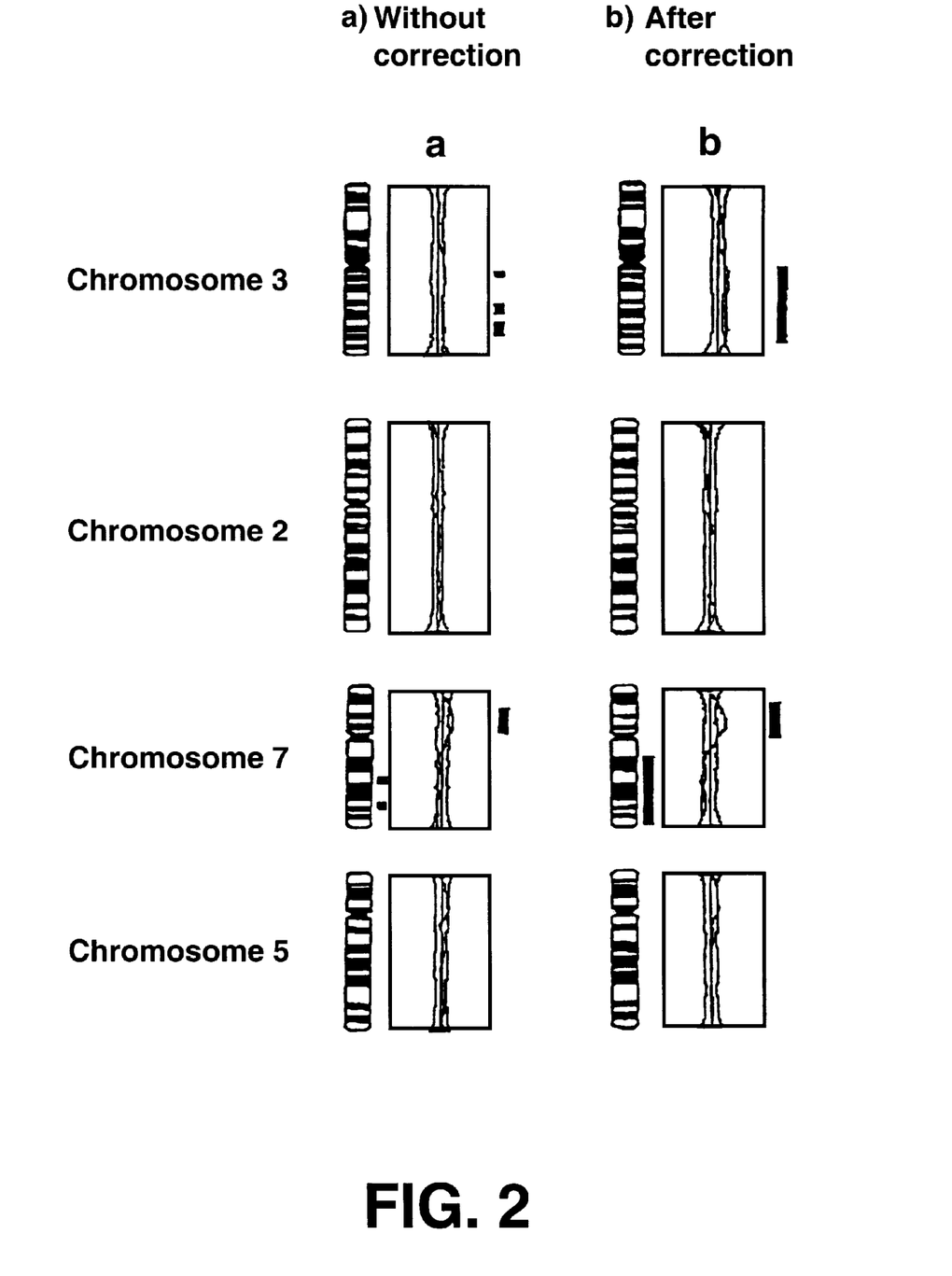
FIG. 2 sets forth an example of a dynamic correction setting forth the ratio profile of testing DNA relative to a reference DNA.
Figure 3A:
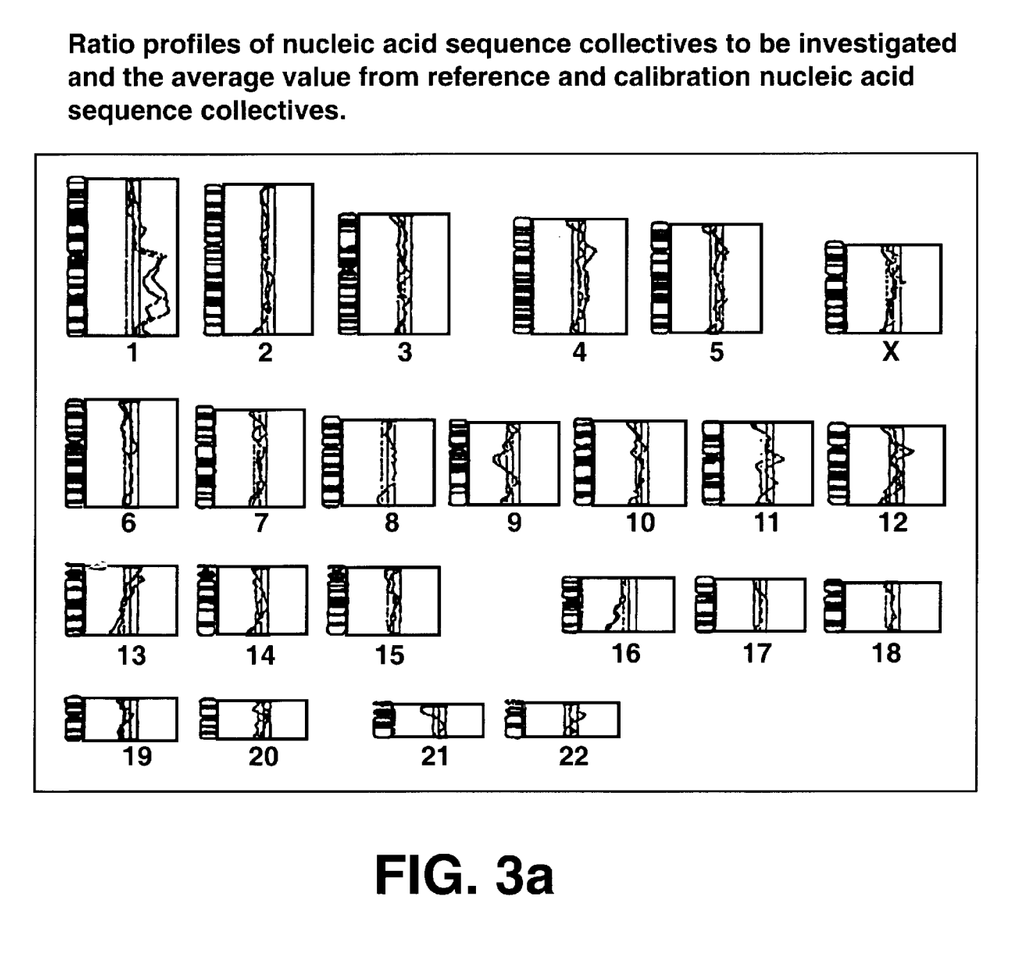
FIG. 3a sets forth ratio profiles of nucleic acid sequence collectives to be investigated and the average value from reference and calibration nucleic acid sequence collectives.
Figure 3B:
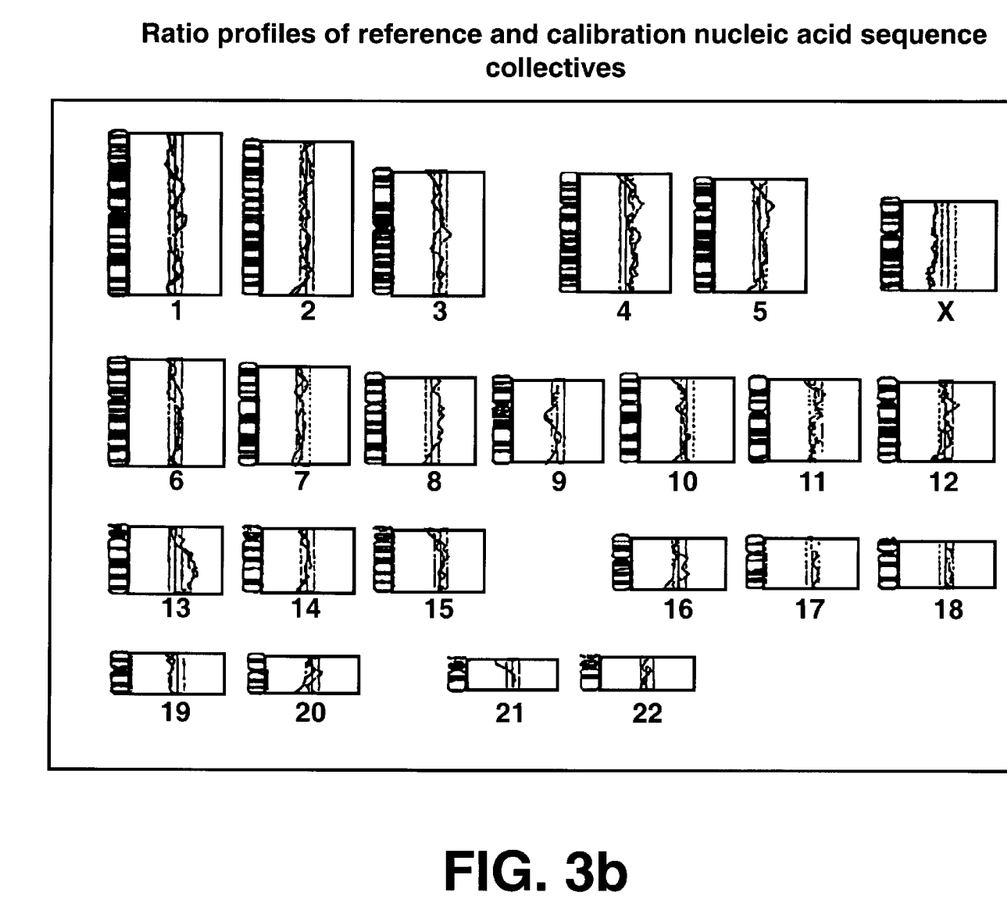
FIG. 3b sets forth profiles of reference and calibration nucleic acid sequence collectives.

FIG. 2 shows an example for a dynamic correction. The ratio profile of testing DNA relative to the average value of calibration-and reference DNA is shown next to the idiogram. The center line corresponds to the ratio value 1, amplifications of the test DNA can be recognized as profile deflections to the right and deletions as profile deflections to the left. The significance boundaries are shown as curves symmetric to the center line. Profile ranges located to the right and to the left of the significance boundaries are interpreted as amplifications and deletions of the test genome. These superthreshold [supraliminal] profile ranges are additionally emphasized by black beams. Chromosome 3 exhibits an amplification 3q running without correction (a) on the boundary of the significance interval. After the dynamic correction (b) has taken place amplification 3q is significant. The normal chromosome 2(at the bottom) remains within the significance boundaries even after the correction.

The simplest possibility of using the additional information of the calibration nucleic acid sequence collective is to show the ratio profiles of test nucleic acid sequence collective compared to reference-and calibration nucleic acid sequence collective on the one hand (FIG. 3a) and to show the ratio profiles of calibration nucleic acid sequence collective compared to reference nucleic acid sequence collective (FIG. 3b) for individual metaphases. The copy number change of the test nucleic acid sequence collective for chromosome 1q can be clearly recognized. Copy number changes (e.g. chromosome 19) located within a range of the significance threshold on account of low quality of the hybridization can also be recognized. The ratio profiles calibration-compared to reference nucleic acid sequence collective (FIG. 3b) should theoretically be approximately 1.0 and 0.5 (X chromosome) and 1.5 (chromosome 13). Chromosome 19 exhibits an hybridization artifact and should not be taken into account for the evaluation. The recognizable deviations (ratio profile X chromosome 0.6 to 0.7, chromosome 13 maximally 1.5) reflect the diminution of dynamics.

Further subject matter of the present invention is constituted by a diagnostic kit for detecting changes in previously defined nucleic acid sequence collectives (T) as target molecules or test DNA, containing at least one reference nucleic acid sequence collective (R) and one calibration nucleic acid sequence collective (S) in accordance with the previous definitions.

The kit in accordance with the invention can be used in particular for detecting and excluding chromosomal changes in human genetics such as balanced chromosomal rearrangements, which are, as is known, of great importance for producing children in the case of carriers of such a change, balanced and unbalanced chromosomal changes as the cause of defects and/or mental retardation and in the diagnosis of tumors, including solid tumors as well as hematological neoplasms (AML. ALL, MDS, etc.), on the one hand for detecting known changes relative to a prognosis and on the other hand for determining further, previously unknown changes.

What is claimed is:

1. A method for determining the relative copy number of nucleic acid sequences of two or more nucleic acid sequences collectives comprising the following steps:

a) labeling
   i) a nucleic acid sequence collective (T) to be investigated;
   ii) a reference nucleic acid sequence collective (R); and
   iii) at least one calibration nucleic acid sequence collective (S) having a known deviation in the copy number of its nucleic acid sequences at at least one known position in comparison to the copy number at the corresponding position of the nucleic acid sequences of the reference nucleic acid sequence collective, said calibration nucleic acid sequence collective being substantially identical to the reference nucleic acid sequence collective, wherein each of said nucleic acid sequence collectives i) to iii) is provided with a different label and hybridizing said nucleic acid sequence collectives i) to iii) to a collective of suitable target nucleic acid sequences;

b) detecting at each position of said nucleic acid sequences the intensity of the labeling of each of said differently labeled nucleic acid sequence collectives i) to iii) being hybridized with said target nucleic acid sequences;

c) determining for said each position a quotient $Q_R$ by dividing the intensity of the labeling of the nucleic acid sequences of said nucleic acid sequence collective to be investigated and the corresponding intensity of the labeling of the nucleic acid sequences of said reference nucleic acid sequence collective:

d) determining for said each position a quotient $Q_S$ by dividing the intensity of the labeling of the nucleic acid sequences of said nucleic acid sequence collective to be investigated and the corresponding intensity of the labeling of the nucleic acid sequences of said calibration nucleic acid sequence collective;

e) determining uncorrected relative copy numbers of the nucleic acid sequences of said nucleic acid sequence collective to be investigated in comparison to the nucleic acid sequences of said reference nucleic acid sequence collective by means of standardizing the quotients $Q_R$ obtained in step c) by dividing the value of $Q_R$ at each position and the value of $Q_R$ which occurs most frequently over all positions;

f) determining uncorrected relative copy numbers of the nucleic acid sequences of said nucleic acid sequence collective to be investigated in comparison to the nucleic acid sequences of said calibration nucleic acid sequence collective by means of standardizing the quotients $Q_S$ obtained in step d) by dividing the value of $Q_S$ at each position through the value of $Q_S$ which occurs most frequently over all positions;

g) determining at least two anchor positions in the nucleic acid sequences of said calibration nucleic acid sequence collective and said reference nucleic acid sequence collective showing a deviation in the amount of the uncorrected relative copy number being equal to said known deviation in the copy number of the nucleic acid sequences of the calibration nucleic acid sequence collective at at least said known position in comparison to the copy number at the corresponding position of the nucleic acid sequences of the reference nucleic acid sequence collective;

h) calculating a correction curve using the deviations between the uncorrected relative copy number at said anchor positions obtained in step g) and corresponding uncorrected relative copy number which are expected due to said known deviation in the copy number of the nucleic acid sequences of the calibration nucleic acid sequence collective in comparison to the copy number of the nucleic acid sequences of the reference nucleic acid sequence collective; and, i) determining final relative copy numbers of the nucleic acid sequences of said nucleic acid sequence collective to be investigated by correcting said uncorrected relative copy numbers obtained in step e) with the aid of said correction curve obtained in step h);

wherein said nucleic acid sequence collectives are selected from the group consisting of mRNA, cDNA, genomic DNA, and-chromosomal DNA.

2. The method according to claim 1 wherein the different label of said nucleic acid sequences of the nucleic acid sequence collectives i) to iii) are different fluorescent dyes and the detecting step b) is carried out by measuring a fluorescence-microscopic signals resulting from the labeled nucleic acid sequences.

3. The method according to claim 1 wherein metaphase chromosomes are used as said collective (T) of said nucleic acid sequence.

4. The method according to claim 1 wherein said collective of said target nucleic acid sequences further comprises isolated nucleic acid sequences arranged on a substrate.

5. The method according to claim 1 wherein said collective of said target nucleic acid sequences further comprises DNA.

6. The method according to claim 1 wherein said collective of said target nucleic acid sequences further comprises cDNA.

7. The method according to claim 1 wherein said reference nucleic acid sequence collective and said calibration nucleic acid sequence are genomic DNA.

8. The method according to claim 1 wherein said nucleic acid sequence collective is selected from a nucleic acid selected from the group consisting of mRNA and cDNA from test cells and said reference nucleic acid sequence collective (R) and said at least one calibration nucleic acid sequence collective (S) are selected from a nucleic acid consisting of the group comprising mRNA and cDNA.

9. The method according to claim 1 wherein repetitive sequences within said nucleic acid sequence collective (T), said reference nucleic acid collective (R), and said at least one calibration nucleic acid sequence collective (S) are suppressed prior to hybridization.

10. The method according to claim 9 wherein said suppression of the repetitive sequences is provided by saturation of the nucleic acid sequences with Cot-1-DNA.

11. The method according to claim 2 wherein said reference nucleic acid sequence collective (R) and said calibration nucleic acid sequence collective (S) are amplified prior to labeling.

12. The method according to claim 1 wherein said at least one calibration nucleic acid sequence is provided by a genome having changes in the copy number in the form of numeric chromosomal aberrations.

13. The method according to claim 1 wherein said at least one calibration nucleic acid sequence collective further comprises a plurality of sequences produced by mixing libraries selected from the group consisting of chromosomes and chromosomal ranges.

14. The method according to claim 1 wherein said known deviations in the copy number of said at least one calibration nucleic acid sequence collective (S) are located at selected sites so that a difference in intensity of the labeling of said calibration sequence (S) with metaphase chromosomes as said nucleic acid sequence collective (T) can additionally be used to distinguish chromosomes.

* * * * *